US012008630B2

(12) United States Patent
Olschan et al.

(10) Patent No.: US 12,008,630 B2
(45) Date of Patent: Jun. 11, 2024

(54) CABINET ELECTRONIC REQUISITION SYSTEM

(71) Applicant: Acme United Corporation, Fairfield, CT (US)

(72) Inventors: Brian S. Olschan, Madison, CT (US); Michael A. Healey, York, ME (US)

(73) Assignee: Acme United Corporation, Shelton, CT (US)

( * ) Notice: Subject to any disclaimer, the term of this patent is extended or adjusted under 35 U.S.C. 154(b) by 631 days.

(21) Appl. No.: 17/126,994

(22) Filed: Dec. 18, 2020

(65) Prior Publication Data

US 2021/0192602 A1 Jun. 24, 2021

Related U.S. Application Data

(60) Provisional application No. 62/950,540, filed on Dec. 19, 2019.

(51) Int. Cl.
| | |
|---|---|
| *G06Q 30/0601* | (2023.01) |
| *A45C 11/00* | (2006.01) |
| *A61B 50/10* | (2016.01) |
| *G06Q 10/087* | (2023.01) |
| *G16H 10/60* | (2018.01) |

(52) U.S. Cl.
CPC .......... *G06Q 30/0635* (2013.01); *A45C 11/00* (2013.01); *G06Q 10/087* (2013.01); *G16H 10/60* (2018.01); *A45C 2011/007* (2013.01); *A61B 50/10* (2016.02)

(58) Field of Classification Search
CPC .. G06Q 30/0635; G06Q 10/60; G06Q 10/087; A45C 2011/007; A45C 11/00; G16H 10/60; A61B 50/10
See application file for complete search history.

(56) References Cited

U.S. PATENT DOCUMENTS

| 59,362 | A | 11/1866 | Comstock |
| 4,673,932 | A | 6/1987 | Ekchian et al. |
| 5,671,362 | A | 9/1997 | Cowe et al. |
| 6,204,764 | B1 | 3/2001 | Maloney |
| 6,232,870 | B1 | 5/2001 | Garber et al. |
| 6,407,665 | B2 | 6/2002 | Maloney |
| 6,539,281 | B2 * | 3/2003 | Wan .................... G07F 17/0092 700/244 |
| 6,707,381 | B1 | 3/2004 | Maloney |
| 6,927,692 | B1 | 8/2005 | Petrinovic |
| 7,175,081 | B2 | 2/2007 | Andreasson et al. |

(Continued)

OTHER PUBLICATIONS

Partial European Search Report.

(Continued)

*Primary Examiner* — Michael Collins
(74) *Attorney, Agent, or Firm* — Alix, Yale & Ristas, LLP

(57) ABSTRACT

A first aid electronic requisition system employs a requisition module located at the first aid cabinet. The requisition module comprises a scanner and an electronic unit in communication with the scanner for transmitting data for remote processing. The compliance cards are associated with the first aid items. In one embodiment, the scanner and electronic unit are powered up upon opening the first aid cabinet. A compliance card is scanned by the scanner and data is remotely transmitted from the module for compiling a requisition order.

9 Claims, 9 Drawing Sheets

(56) References Cited

U.S. PATENT DOCUMENTS

| | | | | |
|---|---|---|---|---|
| 7,178,729 | B2 * | 2/2007 | Shaffer | G06Q 10/087 235/385 |
| 7,348,884 | B2 * | 3/2008 | Higham | G06Q 20/203 700/229 |
| 7,675,421 | B2 * | 3/2010 | Higham | G07F 9/026 700/229 |
| 7,737,858 | B2 | 6/2010 | Matityaho | |
| 8,111,159 | B2 | 2/2012 | Andreasson et al. | |
| 8,242,914 | B2 | 8/2012 | Matityaho et al. | |
| 8,416,080 | B2 * | 4/2013 | Higham | G06K 17/00 235/382 |
| 8,547,203 | B2 | 10/2013 | Sriharto et al. | |
| 8,990,099 | B2 | 3/2015 | MacDonald et al. | |
| 9,013,307 | B2 | 4/2015 | Hussain et al. | |
| 9,037,479 | B1 | 5/2015 | MacDonald et al. | |
| 9,058,412 | B2 | 6/2015 | MacDonald et al. | |
| 9,058,413 | B2 | 6/2015 | MacDonald et al. | |
| 9,189,769 | B2 | 11/2015 | Caputo et al. | |
| 9,268,978 | B2 | 2/2016 | Hussain et al. | |
| 9,324,051 | B2 | 4/2016 | D'Ambrosio et al. | |
| 9,349,030 | B2 | 5/2016 | Elizondo, II | |
| 9,367,665 | B2 | 6/2016 | Macdonald et al. | |
| 9,449,296 | B2 | 9/2016 | MacDonald et al. | |
| 9,552,568 | B2 | 1/2017 | Caputo et al. | |
| 9,558,470 | B2 | 1/2017 | Matityaho | |
| 9,684,766 | B2 | 6/2017 | Caputo | |
| 9,734,294 | B2 | 8/2017 | MacDonald et al. | |
| 9,792,476 | B2 | 10/2017 | Elizondo, II | |
| 9,805,169 | B2 | 10/2017 | MacDonald et al. | |
| 9,842,189 | B2 | 12/2017 | Caputo et al. | |
| 9,870,495 | B2 | 1/2018 | Elizondo, II | |
| 9,916,427 | B2 | 3/2018 | Hussain et al. | |
| 10,002,679 | B2 | 6/2018 | Caputo | |
| 10,019,694 | B2 | 7/2018 | Elizondo, II | |
| 10,095,893 | B2 | 10/2018 | Hussain et al. | |
| 10,128,001 | B2 | 11/2018 | Hussain et al. | |
| 10,210,954 | B2 | 2/2019 | Caputo et al. | |
| 10,290,368 | B2 | 5/2019 | Caputo | |
| 10,580,060 | B2 * | 3/2020 | Olschan | G06Q 10/0875 |
| 10,621,394 | B2 | 4/2020 | Hussain et al. | |
| 10,658,077 | B2 | 5/2020 | Hussain et al. | |
| 10,817,832 | B1 * | 10/2020 | Agrawal | A61B 5/02208 |
| 10,817,833 | B2 | 10/2020 | Matityaho | |
| 11,017,352 | B2 | 5/2021 | MacDonald et al. | |
| 11,030,572 | B2 | 6/2021 | Matityaho | |
| 11,126,802 | B2 | 9/2021 | Hussain et al. | |
| 11,139,075 | B2 | 10/2021 | MacDonald et al. | |
| 11,144,737 | B2 | 10/2021 | Hussain et al. | |
| 11,361,278 | B2 | 6/2022 | Dattamajumdar et al. | |
| 11,557,393 | B2 | 1/2023 | Gitchell et al. | |
| 11,664,105 | B2 | 5/2023 | Yanowitz et al. | |
| 2003/0117281 | A1 | 6/2003 | Sriharto et al. | |
| 2003/0216831 | A1 | 11/2003 | Hart | |
| 2005/0125097 | A1 | 6/2005 | Chudy et al. | |
| 2006/0022827 | A1 * | 2/2006 | Higham | G08B 13/2417 340/572.1 |
| 2006/0192001 | A1 * | 8/2006 | Shaffer | G06Q 10/087 235/382 |
| 2007/0023512 | A1 | 2/2007 | Miller et al. | |
| 2007/0229268 | A1 | 10/2007 | Swan et al. | |
| 2011/0060378 | A1 | 3/2011 | Tuysserkan | |
| 2013/0035950 | A1 | 2/2013 | MacDonald et al. | |
| 2014/0263674 | A1 | 9/2014 | Cerveny | |
| 2014/0372145 | A1 | 12/2014 | MacDonald et al. | |
| 2015/0021356 | A1 | 1/2015 | Witchell et al. | |
| 2015/0105903 | A1 | 4/2015 | Denny | |
| 2015/0287084 | A1 | 10/2015 | Gura et al. | |
| 2017/0300641 | A1 | 10/2017 | Qerim et al. | |
| 2021/0192602 | A1 | 6/2021 | Olschan et al. | |
| 2021/0383323 | A1 | 12/2021 | MacDonald et al. | |
| 2024/0006057 | A1 * | 1/2024 | Edgell | A61F 17/00 |

OTHER PUBLICATIONS

*Kit Check, Inc.* v. *Health Care Logistics, Inc.* Complaint, Dated Dec. 1, 2017; 45 pgs.

*Kit Check, Inc.* v. *Health Care Logistics, Inc.* Docket Report, Dated Jul. 28, 2022; 10 pgs.

European Search Report for European Application No. 21172438.0 filed on May 6, 2021, dated Jan. 26, 2022; 14 pgs.

* cited by examiner

CABINET ELECTRONIC REQUISITION SYSTEM

CROSS-REFERENCE TO RELATED APPLICATION

This application claims the priority of U.S. Provisional Patent Application No. 62/950,540 filed on Dec. 19, 2019, the application of which is incorporated herein in its entirety.

BACKGROUND

This disclosure relates generally to devices and techniques for ensuring that a first aid cabinet is safely stocked with supplies. More particularly, this disclosure relates to systems which employ automatic processing and electronic devices to monitor first aid cabinets and to order and resupply first aid items.

SUMMARY

Briefly stated, an integrated first aid cabinet comprises a first aid cabinet with a multiplicity of first aid items and a requisition module mounted to or located at the cabinet. Compliance cards are associated with the first aid items. The first aid kit is transformable between an opened and a closed position. The requisition module comprises a scanner, an electronic unit in communication with the scanner for transmitting data for remote processing and a power supply for the scanner and the electronic unit. Upon opening the first aid cabinet, the scanner and the electronic unit are powered up. A compliance card is scanned by the scanner. Data from the compliance card is remotely transmitted from the module.

The requisition module is preferably fixed at the bottom of the cabinet. The module has one or more LEDs which indicate whether a scan by the scanner is acceptable or not acceptable. In one embodiment, the requisition module has an audio device which generates an audio signal indicating a scan by the scanner is acceptable or not acceptable.

The compliance cards may be affixed with a barcode or a QR code. In one preferred embodiment, the compliance cards may be affixed with an RFID tag.

A method for requisitioning first aid supplies for a first aid kit comprises removing a compliance card from the first aid kit. The method includes scanning the compliance card at a scanner located at the first aid kit and transmitting scanned data to a remote location. The method further comprises processing the data at a central requisition management unit and compiling a requisition order for first aid supplies.

The step of scanning may further comprise scanning a compliance card with a barcode, a QR code or an RFID tag.

A requisition system for first aid supplies of a first aid cabinet employs a compliance card with an RFID tag associated with the items of the first aid cabinet and comprises reading the RFIDs of the compliance cards for each of the associated items. The requisition system, in one embodiment, involves removing a compliance card from the first aid cabinet. The requisition system further comprises reading each of the RFIDs remaining in the cabinet. The reading data is processed to identify any RFID compliance card that has been removed from the cabinet. A requisition order for first aid supplies based on the data is compiled.

The requisition system, in one embodiment, comprises forwarding supplies identified in the requisition order to a facility where the first aid cabinet is located. The requisition system may also involve reading of the RFIDs for the compliance cards at pre-established times. In one preferred embodiment, reading the RFIDs for the compliance cards occurs upon opening the cabinet and at a pre-established later time.

DETAILED DESCRIPTION

With reference to the drawings, wherein like numerals represent like parts throughout the figures, a cabinet electronic requisition system 10 employs an internet of things (IOT) device in the form of a scanner module 20 that is mounted to and integrated with a first aid cabinet 12. The scanner module 20, as will be described below, functions to obtain first aid supplies inventory data at the cabinet and communicates the data via a customer specific application programming interface (API) key to a portal of a first aid supply management system 40. The electronic requisition system provides for customer managed device access, as well as customer controlled access to the device settings and configuration. The cabinet electronic requisition system integrates with and seamlessly complements pre-existing inventory techniques and processing and overall management to provide a system for ensuring the safety and integrity of the first aid cabinet.

The electronic requisition system provides a secure scanner module which seamlessly integrates with a supply management system 40 (such as disclosed in U.S. Pat. No. 10,580,060) to provide centralized management and tracking and to allow a customer to seamlessly integrate the requisition system with pre-existing cabinets as well as new cabinets as required for a given organization.

Figure 1A:
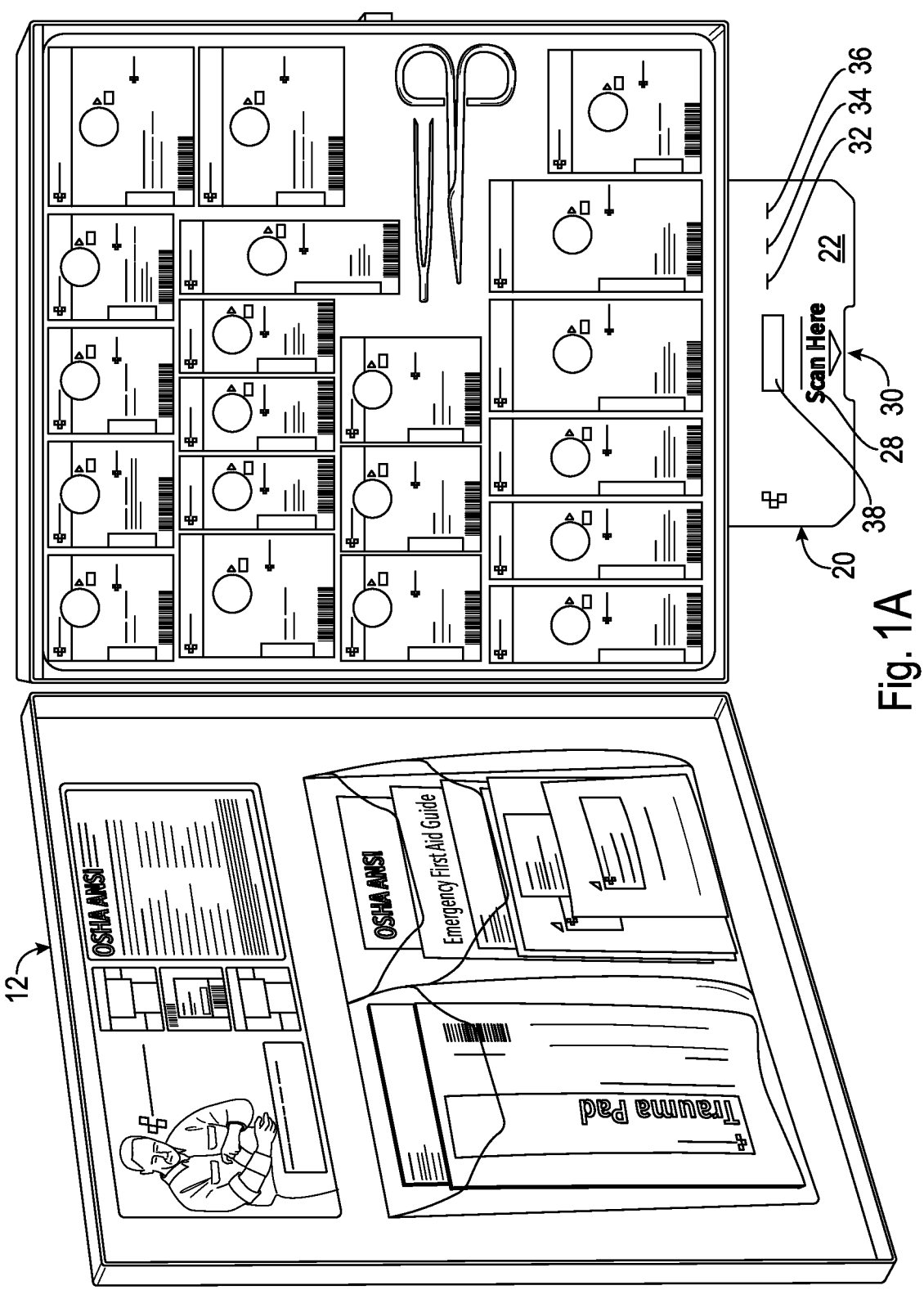
FIG. 1A is a frontal perspective view of a first aid cabinet with an integrated electronic requisition module, the cabinet being illustrated in an opened position.
Figure 1B:
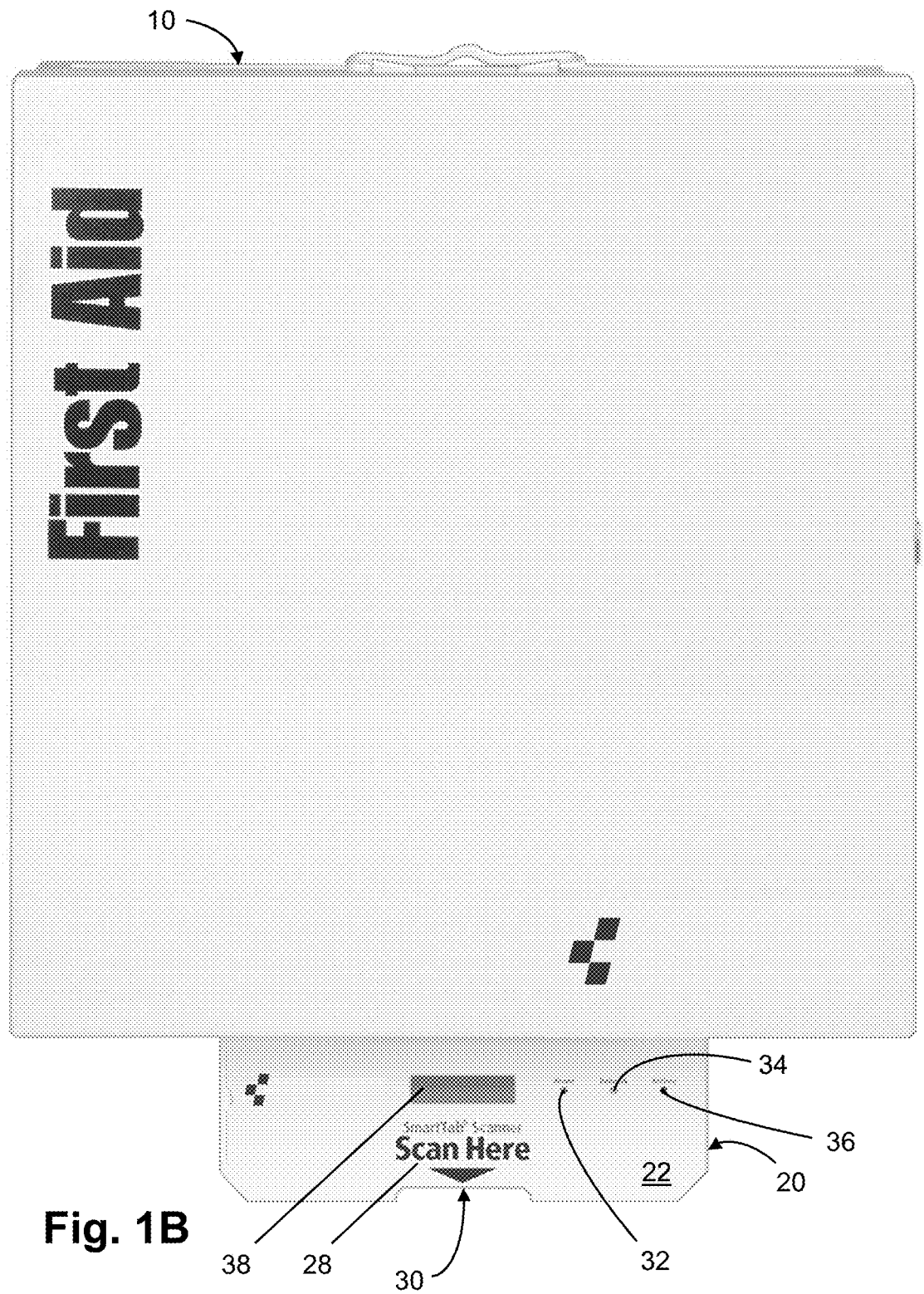
FIG. 1B is a frontal elevational view of the first aid cabinet and integrated requisition module of FIG. 1A, the cabinet being illustrated in a closed position.
Figure 2:
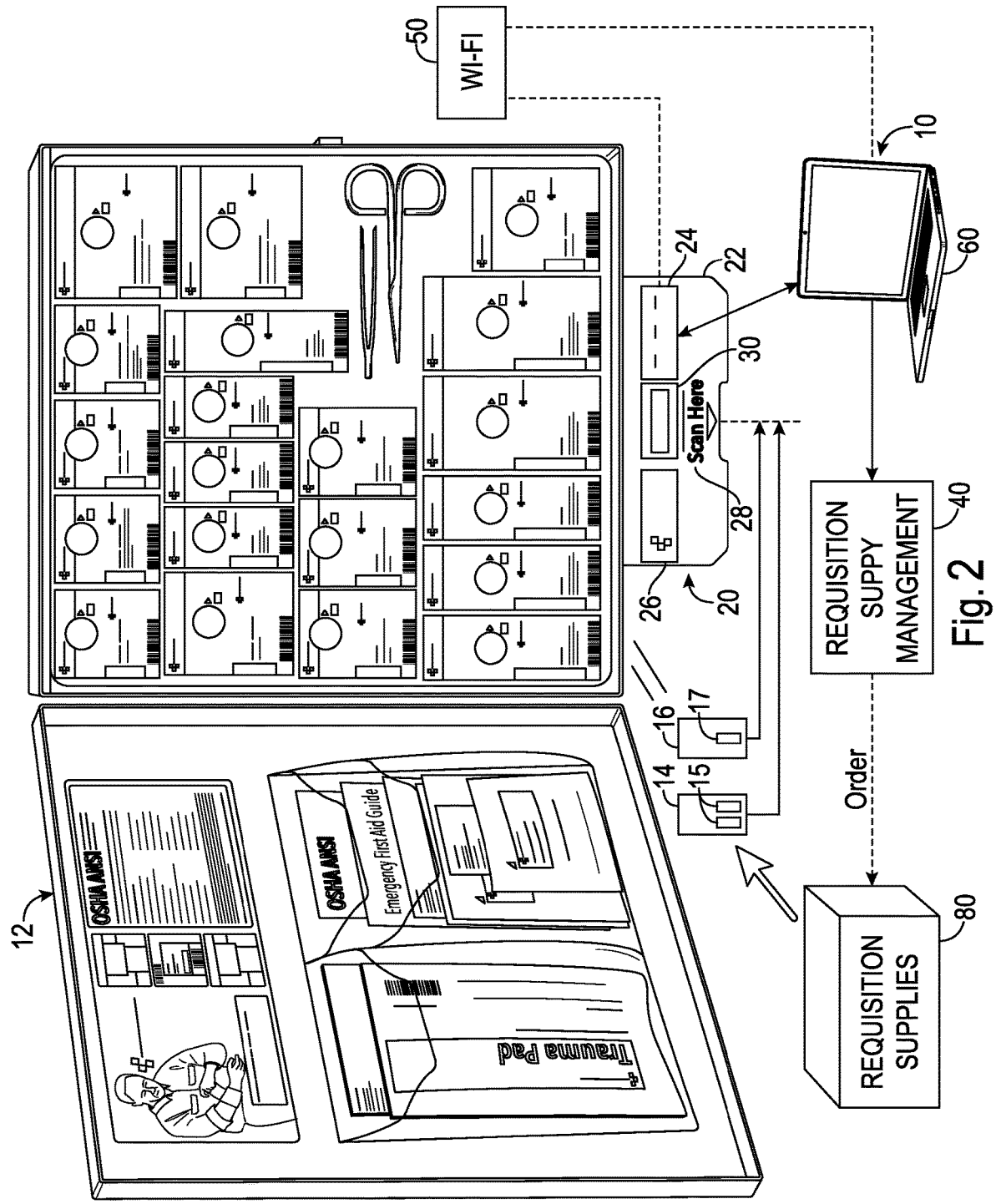
FIG. 2 is a schematic view of the first aid cabinet and integrated requisition module of FIG. 1A further illustrating the operation of the electronic requisition system.

With reference to FIGS. 1A, 1B and 2, an electronic scanner module 20 is mounted at the underside of a first aid cabinet. The module 20 includes a compact housing 22 which houses three principal units. A main circuit board 24 which preferably has dimensions on the order of 5×3×2 inches contains all of the electronics for the requisition module. The main circuit board connects to a battery pack 26 via a cable. The battery pack is preferably on the order of 4×4×2 inches and employs a series of 1.5 or 9 volt batteries to power the requisition module. The main circuit board 24 also connects via a cable with a scanner 30 which is a small footprint LED scanner preferably of a non-laser configuration and may have dimensions of approximately 2×2×1 inches in size.

The front of the unit is affixed with indicia 28 indicating the location of the scan window of the scanner 30 for external scanning. LEDs are also located at the front of the module. LED 32 indicates that the power is on. LED 34 indicates that the wireless connection is okay. LED 36 indicates that the power is low. LED 38 is a scan status indicator wherein a green LED illumination indicates a good (acceptable) scan and a red LED indicator indicates a bad (unacceptable) scan.

The module 20 also preferably emits three core sounds to indicate that a scan is acceptable, a scan is not acceptable and a boot song when the module is powering up.

In a preferred environment, the cabinet 10 is secured to a wall (not illustrated) in an accessible area for the client. The cabinet, and specifically the electronic requisition module, is located in a Wi-Fi accessible network (802.11b/g) 50. It is preferred that the client have a laptop computer 60 to configure the data of the cabinet. The client will also be provided an enterprise code. Each module also has a cabinet validated UPC code. The cabinet is pre-registered via the external management system application 40.

Once the cabinet with the requisition module is installed, the requisition system immediately launches a configuration mode upon boot up. The mode can be accessible at a USB connection from the computer 60 directly to the scanner module 20. The USB port can only be accessed at the back of the module. Once activated, the system requires the following information which can be entered in the computer 60 to enable the requisition system:

1. The serial number of the cabinet which is preferably listed on the side door of each cabinet;
2. Wireless information including the network name and the network password; and
3. The customer enterprise code which is provided by the supplier organization.

The cabinet-to-application integration keys are accessible via an application programming interface (API), user name and an API password. The client sets an access password for future USB access to the scanner module 20.

Pre-existing requisition systems involve refill tags 14 which are typically yellow tags with a barcode 15 or QR code. When the supplies are sufficiently diminished, the refill tag is visible and is removed from the cabinet. In prior systems, the refill tag is then either remotely scanned or forwarded for processing so that the first aid item in question may be replaced.

The present system also allows for a card 16 with an RFID 17 to be removed and scanned by locating the scanner 30 directly at the cabinet 12. The compliance tags 14 or 16 may be efficiently removed and immediately scanned by the scanner 30 at the cabinet 12.

The module 20 also provides for automatic low battery alerts and automatic cabinet status updates. In addition, the cabinet preferably has a feature which requires periodic cabinet checks, such as every seven days, so that the cabinet may be effectively monitored in a consistent manner.

Figure 3A:
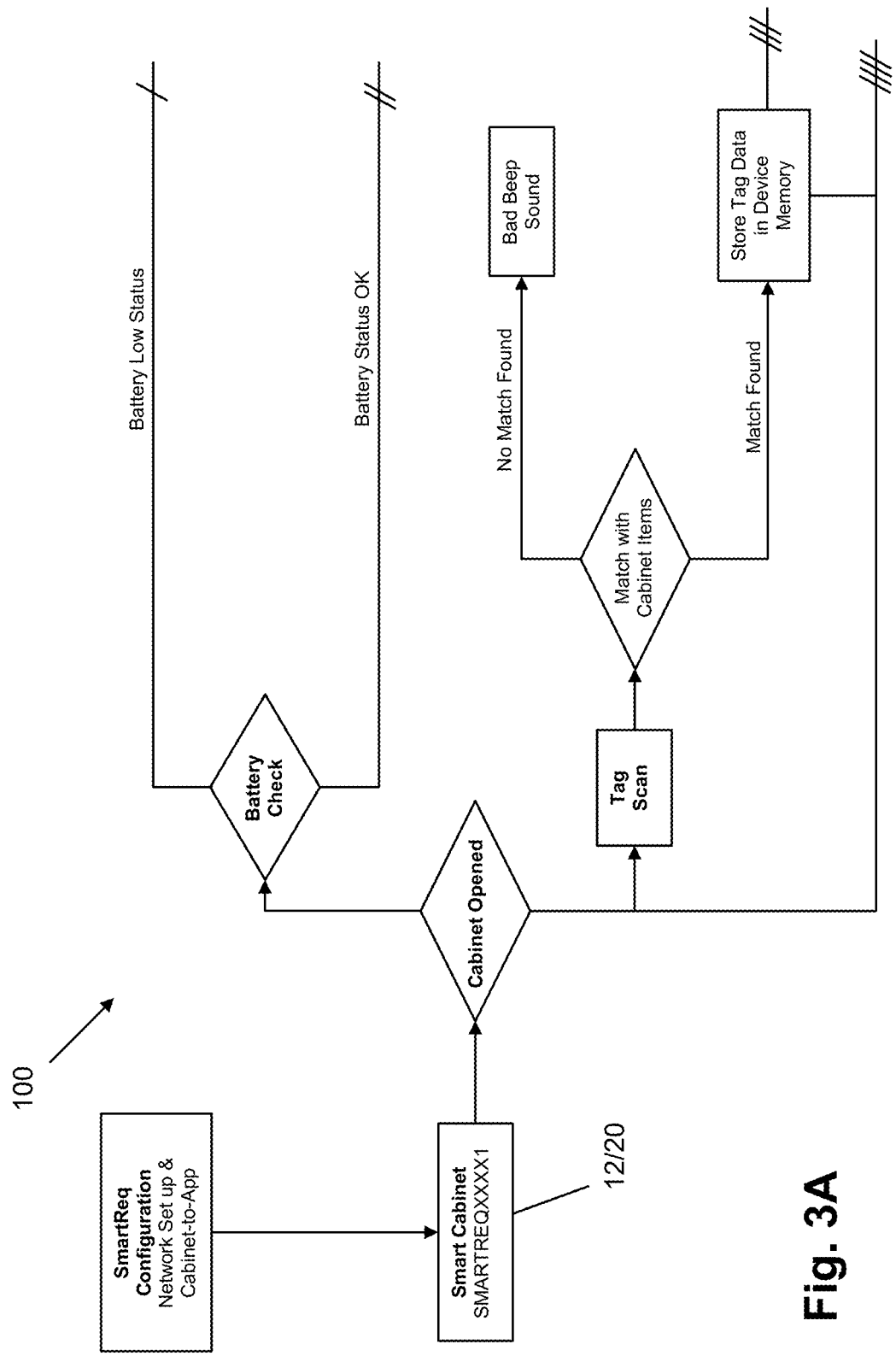
FIGS. 3A-3C together constitute a functional flow diagram for the electronic requisition system which employs the module of FIGS. 1A, 1B and 2.
Figure 3B:
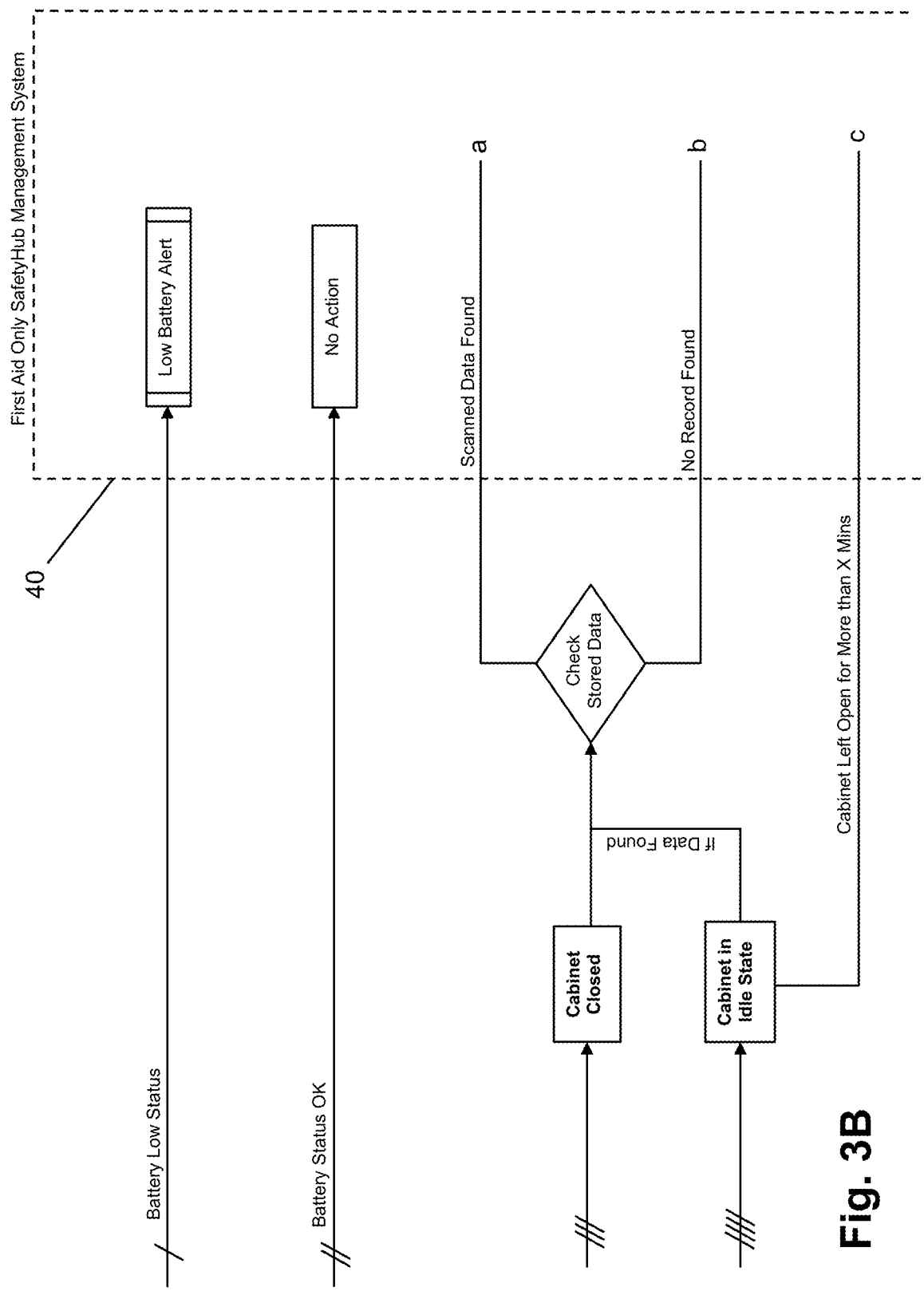
Figure 3C:
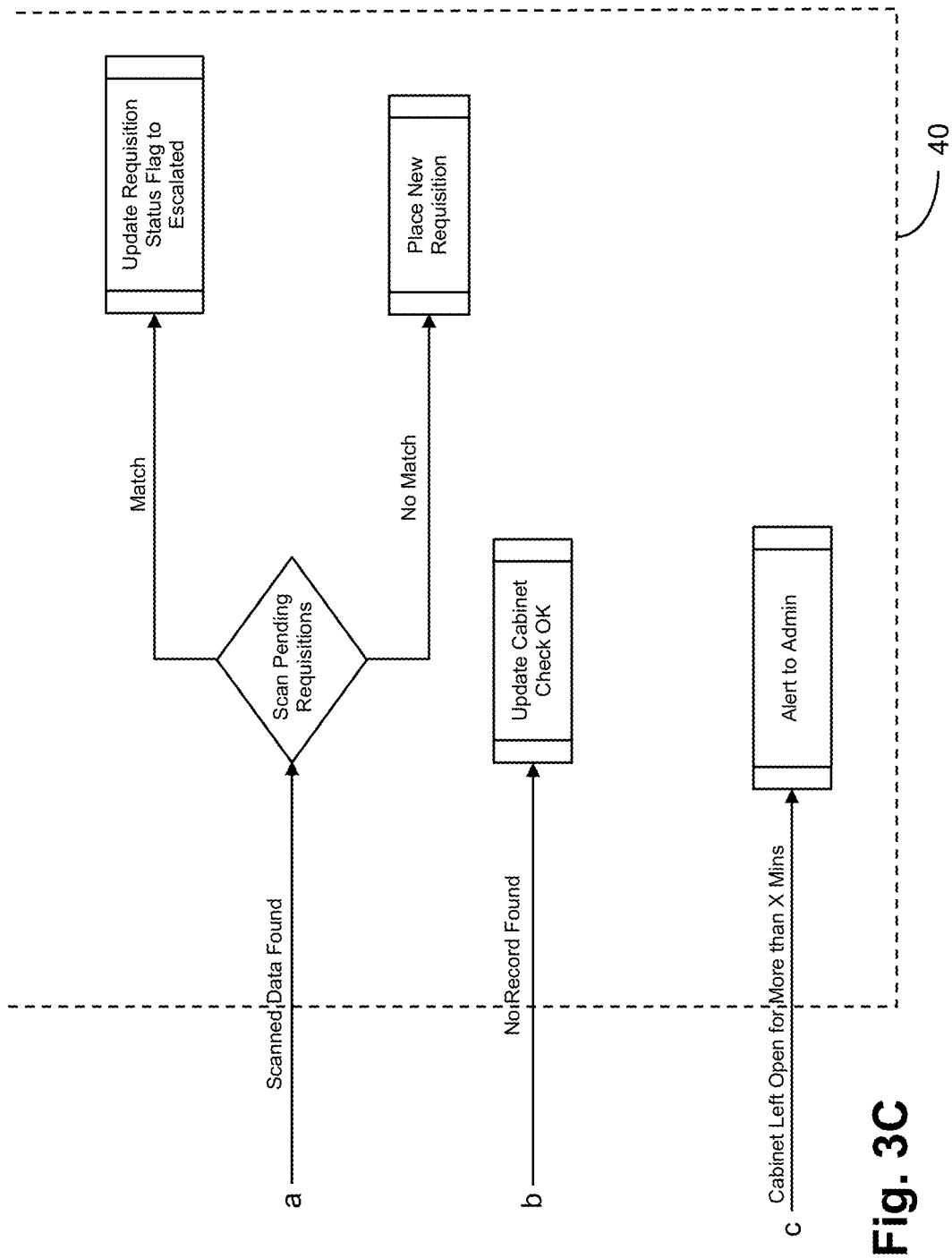

With reference to the overall system of FIGS. 3A-3C, the requisition process in a brief functional block diagram 100 takes place as follows:

1. The user opens the cabinet 12 with the scanner module 20.
2. The system automatically turns on, and a barcode light is illuminated at the bottom of the module.
3. The user scans any missing items as evidenced by the scanning compliance card 14 or 16 on the scanner 30.
4. The scanner module 20 beeps to record each item.
5. Each scanned item is recorded.
6. The items scanned are compared to the table of re-orderable items in that cabinet.
7. Valid requisitions are then transmitted to the back end management system 40.
8. The back end requirements API or email or Excel file is adapted to support the scanned requisition. Once an input is received, the system then surveys for any existing requisition for the item scanned. If the item is determined to be a new item, then a requisition is placed. If an existing requisition is found, an alert is then transmitted that the item is already on a backorder and the existing requisition is expedited.
9. The requisitions are then ultimately managed according to each customer's existing workflow (namely, emailed, downloaded daily, picked up via ERP, etc.) and shipped via a container or package 80 to the cabinet facility. This includes any approval workflow the customer may use to limit small order requests.

Figure 4:
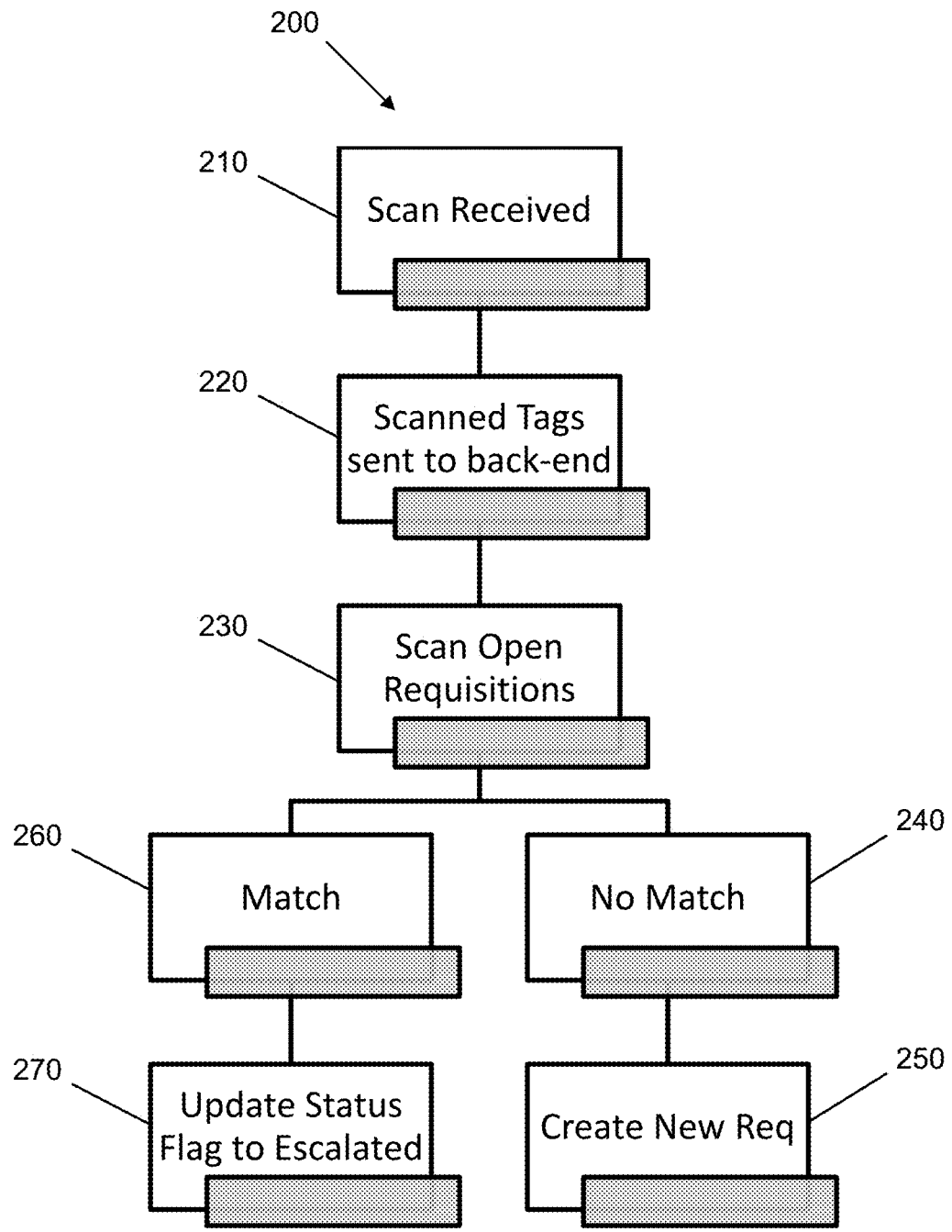
FIG. 4 is a functional flow diagram illustrating a scanning and requisition process for the requisition system.

The back end management system 40 then functions to process the scanned items as illustrated by diagram 200 in FIG. 4. The scan is received at 210. The scanned tag is sent to the back end management system 40 at 220. The scan opens a requisition file at 230. If there is no match at 240, a new requisition is created at 250. If there is a match at 250, an updated status is flagged to expedite the requisition at 270.

Figure 5:
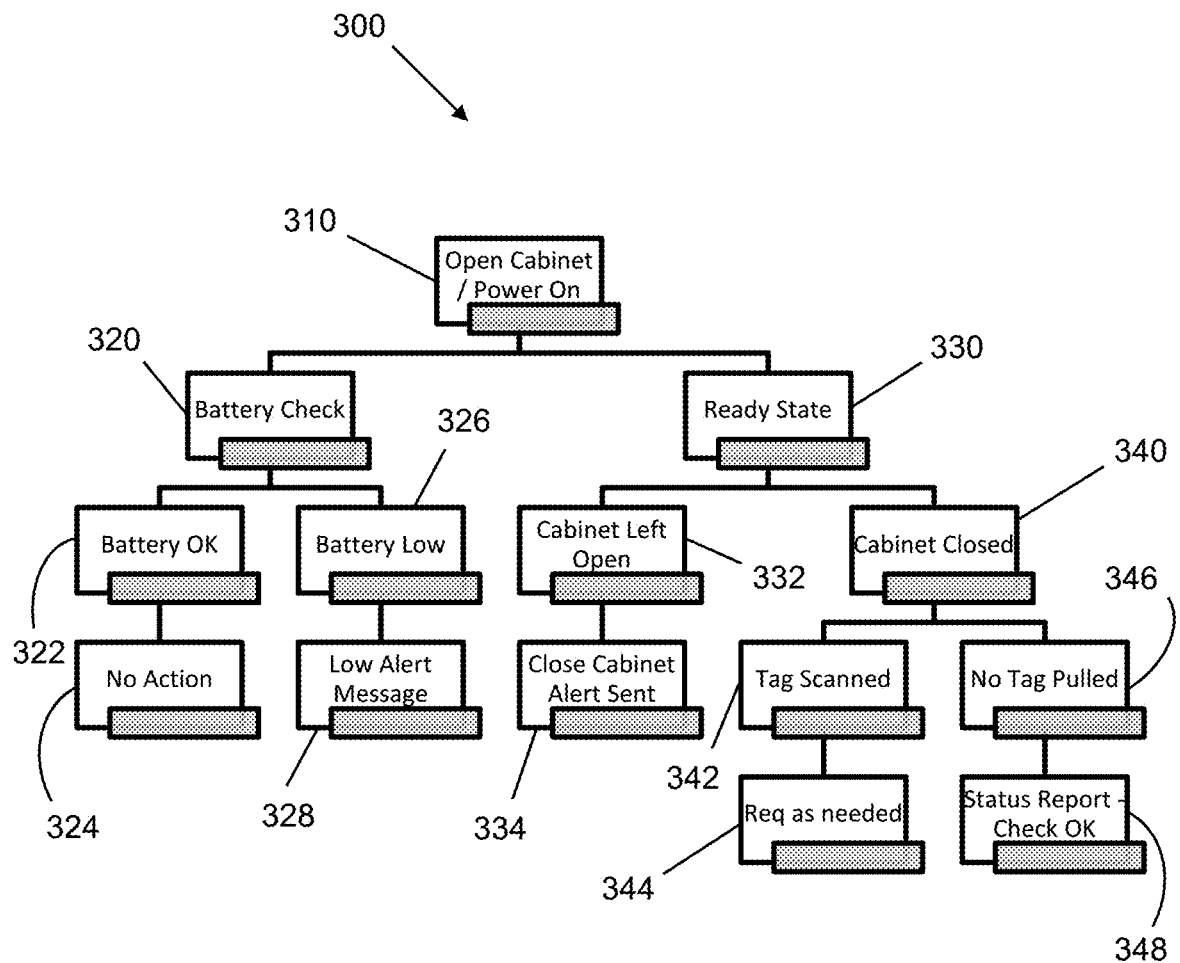
FIG. 5 is a functional flow diagram for a battery employed in the requisition module of FIGS. 1A, 1B and 2.

With reference to FIG. 5, the electronic requisition module employs a battery check process as illustrated by diagram 300. The cabinet is opened and the power is on at 310. The battery is checked at 320. If the battery is okay at 322, no further action is employed at 324. If the battery is low at 326, a low alert message is transmitted at 328. When the cabinet is in the ready state at 330, the cabinet is left open at 332. A closed cabinet alert is sent at 334. When the cabinet is closed at 340, a tag is scanned at 342 and the requisition is made as required at 344. When no tag is pulled at 346, the status report is transmitted to indicate that the status check is okay at 348.

The electronic requisition system requires that the devices, e.g., scanner modules 20 be pre-registered at the back end management app 40 prior to going on site. The administrator creates the IOT device at a laptop computer 60 and registers the cabinet 10 before the requisition scanner module 20 is placed in service.

It is important that cabinets that use the requisition system are configured to require a status check every thirty days. This provides a backup to the standard battery check process and helps identify any Wi-Fi or connectivity issues. If a cabinet is not reported after thirty days, an alert is sent to the designated contacts at the facility for the cabinet as well as to the administrator of the back end management system 40.

Figure 6:
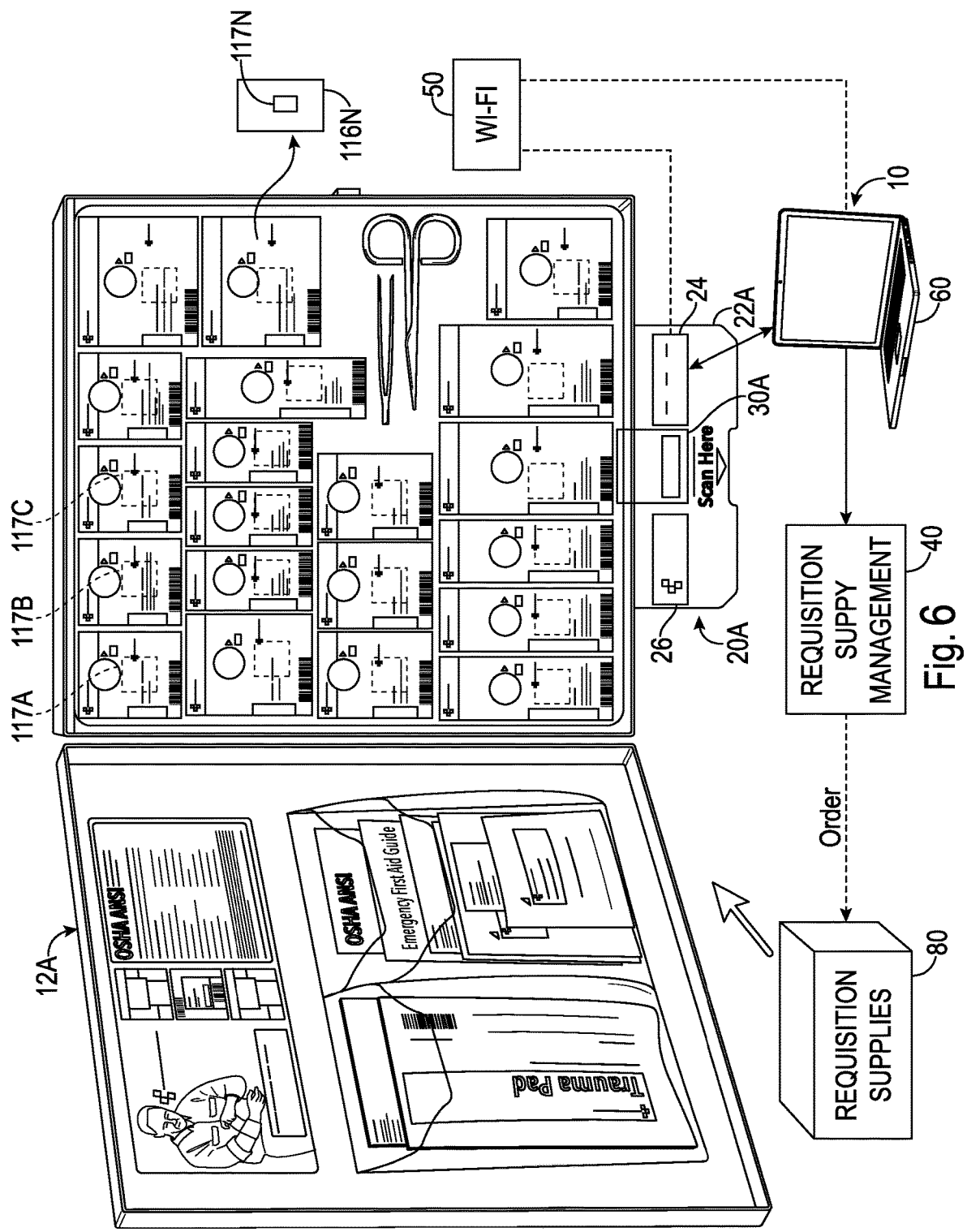
FIG. 6 is a schematic view of a first aid cabinet and a second embodiment of a requisition module illustrating the operation of a second embodiment of an electronic requisition system.

With reference to FIG. 6, a second embodiment of an electronic scanner module 20A is mounted at the underside of a first aid cabinet. The module 20A includes a compact housing 22A which houses three principal components: a main circuit board 24 which contains all the electronics for the requisition module. The main circuit board connects to a battery pack 26 with a cable, as previously described. The main circuit board 24 also connects via cable with a scanner 30A in the form of an RFID reader which is configured so that it reads compliance card RFIDs 117A, 117B, 117C, 117D . . . which are associated with each of the items at the interior of the cabinet. The reader reads each of the RFIDs 117A, 117B, 117C, 117D . . . and transmits same via WI-FI 50 to the requisition supply management system.

When a compliance card 116N with an RFID 117N is removed, such as schematically illustrated in FIG. 6, the system records the removal of the RFID card 116N for the associated item via the reader 30A and data concerning same is sent via WI-FI 50 to the requisition supply management system 40. In all other significant aspects, the requisition system 12A is the same as previously described for requisition system 12. The scanner or reader 30A may read all RFIDs in the cabinet at pre-established intervals or upon opening the cabinet and at a subsequent time interval thereafter.

With the installation of the requisition module, the cabinet indicates that this is a self-ordering unit and requires the cabinet model, the serial number and the location detail. The requisition user module itself is created as a virtual user which requires assuming the same roles as someone ordering the app including tracking requisitions by devices. Each of the requisition modules 20 and 20A preferably use a format which includes a name, a location and client location, and an email address for the specific modules.

While preferred embodiments of the foregoing have been set forth for purposes of illustration, the foregoing description should not be deemed a limitation of the invention herein. Accordingly, various modifications, adaptations and alternatives may occur to one skilled in the art without departing from the spirit and the scope of the present invention.

The invention claimed is:

1. A requisition system for first aid items of a first aid cabinet having a compliance card with an RFID associated with the first aid items of the first aid cabinet comprising:
    a) generating a first data set including first aid items in the first aid cabinet, each first aid item associated with a compliance card with an RFID;
    b) removing a compliance card from the first aid cabinet when the first aid items associated with the compliance card reach a pre-determined minimum number of the first aid items associated with the compliance card, with the pre-determined minimum number of first aid items associated with the compliance card remaining in the cabinet;
    c) reading each of the RFIDs of the compliance cards remaining in the cabinet and generating a second data set;
    d) processing said first data set and said second data set to identify any compliance card that has been removed from the cabinet and generating supply data for the first aid items associated with each compliance card removed from the cabinet; and
    e) compiling a requisition order for first aid items based on said supply data.

2. The requisition system of claim 1 further comprising transferring supplies identified in the order to a facility where the first aid cabinet is located.

3. The requisition system of claim 1 wherein said reading of the RFIDs for the compliance cards is accomplished at pre-established times.

4. The requisition system of claim 1 wherein said reading of the RFIDs for the compliance cards occurs upon opening the cabinet and at a pre-established later time.

5. The requisition system of claim 1, wherein said step of generating a first data set includes reading the RFIDs of the compliance cards for each of the associated first aid items included in the first aid cabinet.

6. The requisition system of claim 1, comprising arranging the compliance cards associated with each first aid item to be visible when the associated first aid items are exhausted or reach a pre-determined minimum number.

7. The requisition system of claim 1, comprising managing the requisition orders according to a workflow established by an owner of the first aid cabinet.

8. The requisition system of claim 1, comprising equipping the first aid cabinet with an RFID scanner configured to read the RFIDs on compliance cards in the first aid cabinet.

9. The requisition system of claim 1, comprising:
    equipping the first aid cabinet with an RFID scanner configured to read the RFIDs on compliance cards in the first aid cabinet;
    equipping the first aid cabinet with WiFi; and
    transmitting the requisition order from the first aid cabinet using WiFi.

* * * * *